US011021951B2

(12) United States Patent
Olapade et al.

(10) Patent No.: US 11,021,951 B2
(45) Date of Patent: Jun. 1, 2021

(54) CONTAMINATION PREDICTION OF DOWNHOLE PUMPOUT AND SAMPLING

(71) Applicant: Halliburton Energy Services, Inc., Houston, TX (US)

(72) Inventors: Peter Ojo Olapade, Richmond, TX (US); Bin Dai, Spring, TX (US); Christopher Michael Jones, Katy, TX (US); James Martin Price, Cypress, TX (US); Dingding Chen, Tomball, TX (US); Anthony Herman Van Zuilekom, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 49 days.

(21) Appl. No.: 16/447,808

(22) Filed: Jun. 20, 2019

(65) Prior Publication Data

US 2020/0400017 A1 Dec. 24, 2020

(51) Int. Cl.
  *E21B 49/08* (2006.01)
  *E21B 49/10* (2006.01)
  *E21B 47/06* (2012.01)
  *G01N 33/28* (2006.01)
  (Continued)

(52) U.S. Cl.
  CPC ............ *E21B 49/081* (2013.01); *E21B 47/06* (2013.01); *E21B 49/10* (2013.01); *G01N 33/2823* (2013.01); *E21B 21/003* (2013.01); *E21B 47/12* (2013.01); *E21B 49/0875* (2020.05)

(58) Field of Classification Search
  CPC ............................. E21B 49/10; E21B 49/088
  See application file for complete search history.

(56) References Cited

U.S. PATENT DOCUMENTS 6,274,865 B1 8/2001 Schroer et al.
7,595,876 B2 9/2009 DiFoggio
(Continued)

FOREIGN PATENT DOCUMENTS

GB 2467484 8/2010

OTHER PUBLICATIONS

Halliburton, GeoTap IDS Fluid Identification and Sampling Sensor,Logging While Drilling, H013251, Jun. 2019.
(Continued)

*Primary Examiner* — Shane Bomar
(74) *Attorney, Agent, or Firm* — John Wustenberg; C.Tumey Law Group PLLC

(57) ABSTRACT

A method may comprise positioning a downhole fluid sampling tool into a wellbore, performing a pressure test operation within the wellbore, performing a pumpout operation within the wellbore, identifying when a clean fluid sample may be taken by the downhole fluid sampling tool from at least the pressure test operation and the pumpout operation, and acquiring the clean fluid sample from the wellbore. A system may comprise a downhole fluid sampling tool and an information handling machine. The downhole fluid sampling tool may further comprise one or more probes attached to the downhole fluid sampling tool, one or more stabilizers attached to the downhole fluid sampling tool, and a sensor placed in the downhole fluid sampling tool configured to measure drilling fluid filtrate.

22 Claims, 4 Drawing Sheets

(51) Int. Cl.
*E21B 21/00* (2006.01)
*E21B 47/12* (2012.01)

(56) References Cited

U.S. PATENT DOCUMENTS

| | | | |
|---|---|---|---|
| 8,528,396 B2* | 9/2013 | Wu | E21B 49/082 |
| | | | 73/152.55 |
| 8,744,774 B2 | 6/2014 | Zazovsky | |
| 2004/0231842 A1 | 11/2004 | Shammai et al. | |
| 2007/0214877 A1* | 9/2007 | Shammai | E21B 49/10 |
| | | | 73/152.24 |
| 2010/0294491 A1* | 11/2010 | Zazovsky | E21B 49/087 |
| | | | 166/250.01 |
| 2011/0048700 A1* | 3/2011 | van Zuilekom | G01N 9/00 |
| | | | 166/250.01 |
| 2011/0320127 A1 | 12/2011 | Zazovsky et al. | |
| 2013/0311099 A1* | 11/2013 | Eyuboglu | E21B 49/08 |
| | | | 702/11 |
| 2015/0226059 A1* | 8/2015 | Zuo | G01N 33/2835 |
| | | | 73/152.18 |
| 2016/0090836 A1 | 3/2016 | Wang et al. | |
| 2016/0186562 A1 | 6/2016 | Lee et al. | |
| 2016/0216404 A1 | 7/2016 | Kristensen et al. | |
| 2017/0074095 A1 | 3/2017 | Nguyen-Thuyet | |
| 2017/0356896 A1 | 12/2017 | Anand | |
| 2017/0370214 A1 | 12/2017 | Wang et al. | |
| 2018/0371903 A1* | 12/2018 | Li | E21B 49/008 |
| 2019/0227191 A1* | 7/2019 | Raman | G01N 33/2823 |
| 2020/0370418 A1* | 11/2020 | Fries | G01V 11/002 |

OTHER PUBLICATIONS

Halliburton, Halliburton Reservoir Description Tool (RDT) Formation Tester, Formation Evaluation, H012350, Nov. 2016.
Baker Hughes, RCI and IFX Systems provide real-time fluid data and analysis in the North Sea, 2017.
Schlumberger, MDT Modular Formation Dynamics Tester, SMP-5124, Jun. 2002.
Sami Eyuboglu, et al., A New Real-Time Contamination Method that Combines Multiple Sensor Technologies, SPWLA 52nd Annual Logging Symposium, May 14-18, 2011.
International Search Report and Written Opinion, Application No. PCT/US2019/038340, dated Mar. 18, 2020.
Andrews et al., "Quantifying contamination using color of crude and condensate", 2016 Oilfield Review (see p. 24).

* cited by examiner

CONTAMINATION PREDICTION OF DOWNHOLE PUMPOUT AND SAMPLING

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation. One technique for collecting relevant information involves collecting a formation fluid sample at any specified depth within a wellbore. The acquisition of representative formation fluid samples is essential for proper reservoir management and development. However, because of overbalance pressure in the mud column, mud filtrate invades and contaminates the reservoir fluid during the drilling process, before the mudcake around the wellbore is properly formed.

Currently, methods and systems for identifying and capturing clean formation fluid samples can be limited by pumpout data identified during a pumpout operation. Additionally, current methods and systems can use curve fitting methods to determine when a clean fluid sample may be taken at a moment in time. However, curve fitting methods can rely on the assumption that when the properties being monitored does not change significantly as the pumping continues, the contamination level is low. However, this may also be because of steady state effect even at high contamination levels.

BRIEF DESCRIPTION OF THE DRAWINGS

These drawings illustrate certain aspects of some of the examples of the present disclosure, and should not be used to limit or define the disclosure.

DETAILED DESCRIPTION

This disclosure is directed to subterranean operations and, more particularly, to methods for operating a downhole formation testing tool to capture clean sample fluids after preforming a pressure test operation and a pumpout operation. By utilizing the measurements and properties found during the pressure test operation and the pumpout operation, the time at which it may be possible to capture a clean fluid may be identified.

Figure 1:
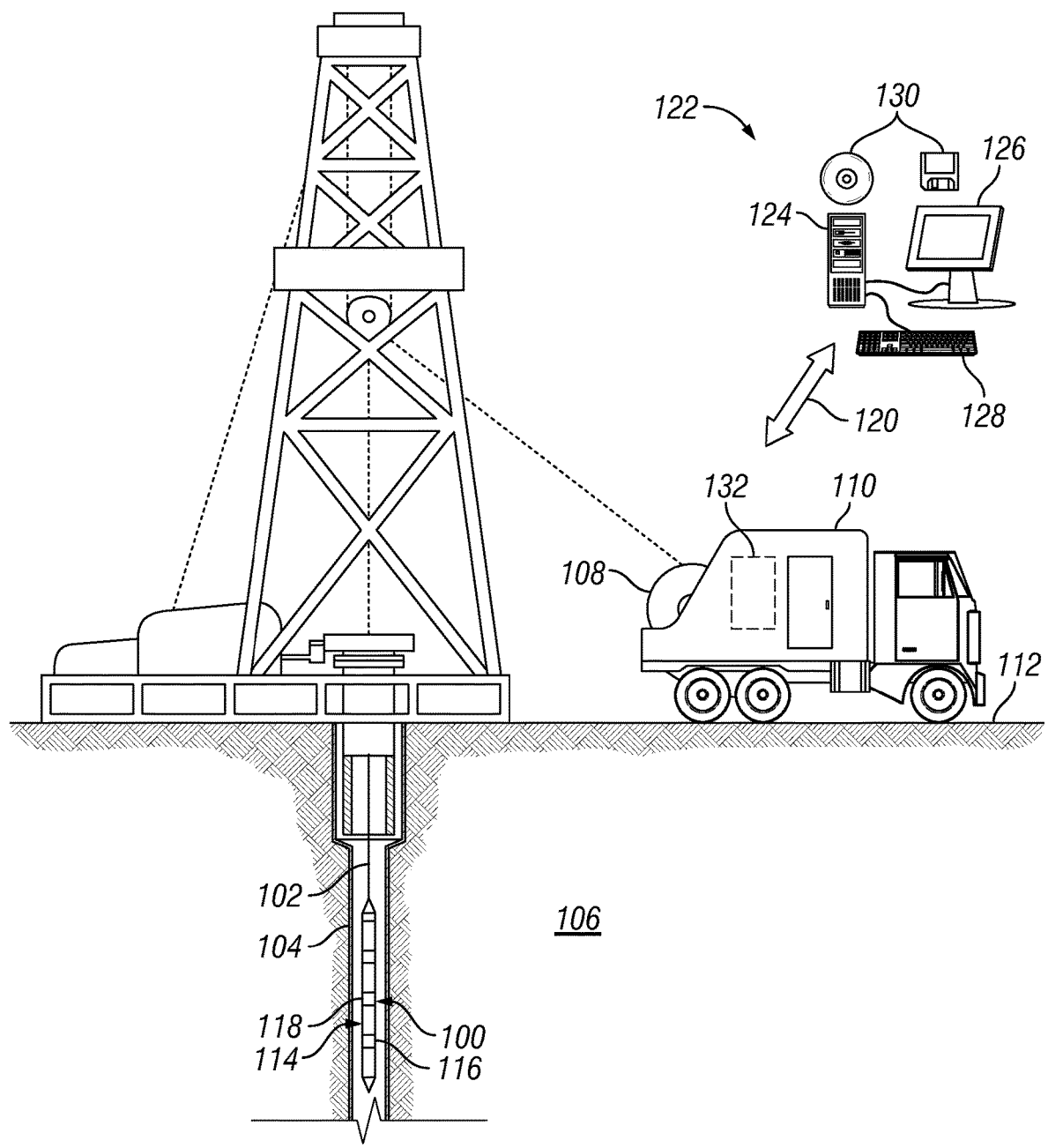
FIG. 1 is a schematic diagram of an example of a formation testing tool on a wireline.

FIG. 1 is a schematic diagram of formation testing tool 100 on a conveyance 102 in accordance with example embodiment. As illustrated, wellbore 104 may extend through subterranean formation 106. In examples, reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run formation testing tool 100 into wellbore 104. Hoist 108 may be disposed on a vehicle 110. Hoist 108 may be used, for example, to raise and lower conveyance 102 in wellbore 104. While hoist 108 is shown on vehicle 110, it should be understood that conveyance 102 may alternatively be disposed from a hoist 108 that is installed at surface 112 instead of being located on vehicle 110. Formation testing tool 100 may be suspended in wellbore 104 on conveyance 102. Other conveyance types may be used for conveying formation testing tool 100 into wellbore 104, including coiled tubing and wired drill pipe, for example. Formation testing tool 100 may include a tool body 114, which may be elongated as shown on FIG. 1. Tool body 114 may be any suitable material, including without limitation titanium, stainless steel, alloys, plastic, combinations thereof, and the like. Formation testing tool 100 may further include one or more sensors 116 for measuring properties of the fluid sample, reservoir fluid, wellbore 104, subterranean formation 106, or the like. In examples, formation testing tool 100 may also include a fluid analysis module 118, which may be operable to process information regarding fluid sample, as described below. Formation testing tool 100 may be used to collect fluid samples from subterranean formation 106 and may obtain and separately store different fluid samples from subterranean formation 106.

In examples, fluid analysis module 118 may include at least one sensor that may continuously monitor a reservoir fluid. Such sensors include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors. Sensors may measure a contrast between drilling fluid filtrate properties and formation fluid properties.

In examples, fluid analysis module 118 may be a gas chromatography analyzer (GC). A gas chromatography analyzer may separate and analyze compounds that may be vaporized without decomposition. Fluid samples from wellbore 104 may be injected into a GC column and vaporized. Different compounds may be separated due to their retention time difference in the vapor state. Analyses of the compounds may be displayed in GC chromatographs. In examples, a mixture of formation fluid and drilling fluid filtrate may be separated and analyzed to determine the properties within the formation fluid and drilling fluid filtrate.

Fluid analysis module 118 may be operable to derive properties and characterize the fluid sample. By way of example, fluid analysis module 118 may measure absorption, transmittance, or reflectance spectra and translate such measurements into component concentrations of the fluid sample, which may be lumped component concentrations, as described above. The fluid analysis module 118 may also measure gas-to-oil ratio, fluid composition, water cut, live fluid density, live fluid viscosity, formation pressure, and formation temperature. Fluid analysis module 118 may also be operable to determine fluid contamination of the fluid sample and may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 118 may include random access memory (RAM), one or more processing units, such as a central processing unit (CPU), or hardware or software control logic, ROM, and/or other types of nonvolatile memory.

Any suitable technique may be used for transmitting signals from the formation testing tool 100 to surface 112. As illustrated, a communication link 120 (which may be wired or wireless, for example) may be provided that may transmit data from formation testing tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. Information handling system 122 may act as a data acquisition system and possibly a data processing system that analyzes information from formation testing tool 100. For example, information handling system 122 may process the information from formation testing tool 100 for determination of fluid contamination. Information handling system 122 may also determine additional properties of the fluid sample (or reservoir fluid), such as component concentrations, pressure-volume-temperature properties (e.g., bubble point, phase envelop prediction, etc.) based on the fluid characterization. This processing may occur at surface 112 in real-time. Alternatively, the processing may occur downhole hole or at surface 112 or another location after recovery of formation testing tool 100 from wellbore 104. Alternatively, the processing may be performed by an information handling system in wellbore 104, such as fluid analysis module 118. The resultant fluid contamination and fluid properties may then be transmitted to surface 112, for example, in real-time.

It should be noted that in examples a gas chromatographer 132 may be disposed on surface 112 and analyze samples captures by formation testing tool 100. For example, fluid analysis module 118 may capture fluid samples and bring them to the surface 112 for analysis at the wellsite. As illustrated, gas chromatographer 132 may be disposed in vehicle 110. However, gas chromatographer 132 may be a standalone assembly that may be available at the wellsite. Additionally, information handling system 122 may be connected to gas chromatographer 132 through communication link 120. In examples, gas chromatographer 132 may operate and function as described above.

Figure 2:
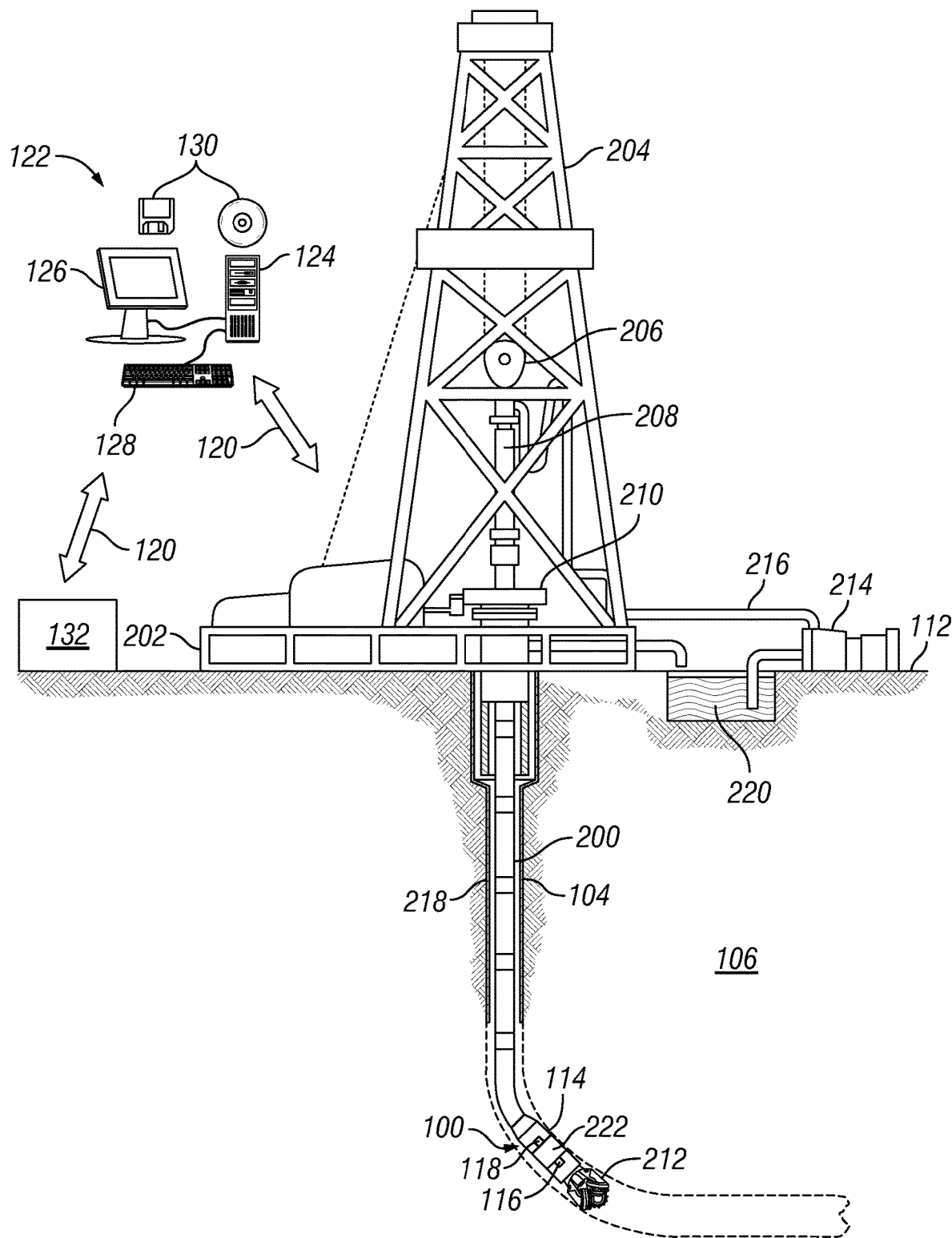
FIG. 2 is a schematic diagram of an example of the formation testing tool on a drill string.

Referring now to FIG. 2, a schematic diagram is shown of formation testing tool 100 disposed on a drill string 200 in a drilling operation in accordance with example embodiments. Formation testing tool 100 may be used to obtain a fluid sample, for example, a fluid sample of a reservoir fluid from subterranean formation 106. The reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 2 shows a vertical or low inclination angle well, high inclination angle or horizontal placement of the well and equipment is also possible. It should further be noted that while FIG. 2 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 202 may support a derrick 204 having a traveling block 206 for raising and lowering drill string 200. Drill string 200 may include, but is not limited to, drill pipe and coiled tubing, as generally known to those skilled in the art. A kelly 208 may support drill string 200 as it may be lowered through a rotary table 210. A drill bit 212 may be attached to the distal end of drill string 200 and may be driven either by a downhole motor and/or via rotation of drill string 200 from the surface 112. Without limitation, drill bit 212 may include, roller cone bits, PDC bits, natural diamond bits, any hole openers, reamers, coring bits, and the like. As drill bit 212 rotates, it may create and extend wellbore 104 that penetrates various subterranean formations 106. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and formation testing tool 100. Formation testing tool 100, which may be built into the drill collars 22) may gather measurements and fluid samples as described herein. One or more of the drill collars 222 may form a tool body 114, which may be elongated as shown on FIG. 2. Tool body 114 may be any suitable material, including without limitation titanium, stainless steel, alloys, plastic, combinations thereof, and the like. Formation testing tool 100 may be similar in configuration and operation to formation testing tool 100 shown on FIG. 1 except that FIG. 2 shows formation testing tool 100 disposed on drill string 200. Alternatively, the sampling tool may be lowered into the wellbore after drilling operations on a wireline.

Formation testing tool 100 may further include one or more sensors 116 for measuring properties of the fluid sample reservoir fluid, wellbore 104, subterranean formation 106, or the like. The properties of the fluid are measured as the fluid passes from the formation through the tool and into either the wellbore or a sample container. As fluid is flushed in the near wellbore region by the mechanical pump, the fluid that passes through the tool generally reduces in drilling fluid filtrate content, and generally increases in formation fluid content. Formation testing tool 100 may be used to collect a fluid sample from subterranean formation 106 when the filtrate content has been determined to be sufficiently low. Sufficiently low depends on the purpose of sampling. For some laboratory testing below 10% drilling fluid contamination is sufficiently low, and for other testing below 1% drilling fluid filtrate contamination is sufficiently low. Sufficiently low also depends on the nature of the formation fluid such that lower requirements are generally needed, the lighter the oil as designated with either a higher GOR or a higher API gravity. Sufficiently low also depends on the rate of cleanup in a cost benefit analysis since longer pumpout times required to incrementally reduce the contamination levels may have prohibitively large costs. As previously described, the fluid sample may include a reservoir fluid, which may be contaminated with a drilling fluid or drilling fluid filtrate. Formation testing tool 100 may obtain and separately store different fluid samples from subterranean formation 106 with fluid analysis module 118. Fluid analysis module 118 may operate and function in the same manner as described above. However, storing of the fluid samples in the formation testing tool 100 may be based on the determination of the fluid contamination. For example, if the fluid contamination exceeds a tolerance, then the fluid sample may not be stored. If the fluid contamination is within a tolerance, then the fluid sample may be stored in the formation testing tool 100.

As previously described, information from formation testing tool 100 may be transmitted to an information handling system 122, which may be located at surface 112. As illustrated, communication link 120 (which may be wired or wireless, for example) may be provided that may transmit data from formation testing tool 100 to an information handling system 111 at surface 112. Information handling system 140 may include a processing unit 124, a monitor 126, an input device 128 (e.g., keyboard, mouse, etc.), and/or computer media 130 (e.g., optical disks, magnetic disks) that may store code representative of the methods described herein. In addition to, or in place of processing at surface 112, processing may occur downhole (e.g., fluid analysis module 118). In examples, information handling system 122 may perform computations to estimate clean fluid composition.

As previously described above, a gas chromatographer 132 (e.g., referring to FIG. 1) may be disposed on surface 112 and analyze samples captures by downhole fluid sampling tool 100. For example, fluid analysis module 118 may capture fluid samples and bring them to the surface 112 for analysis at the wellsite. As illustrated, gas chromatographer 132 may be a standalone assembly that may be available at the wellsite. Additionally, information handling system 122 may be connected to gas chromatographer 132 through communication link 120. In examples, gas chromatographer 132 may operate and function as described above.

Figure 3:
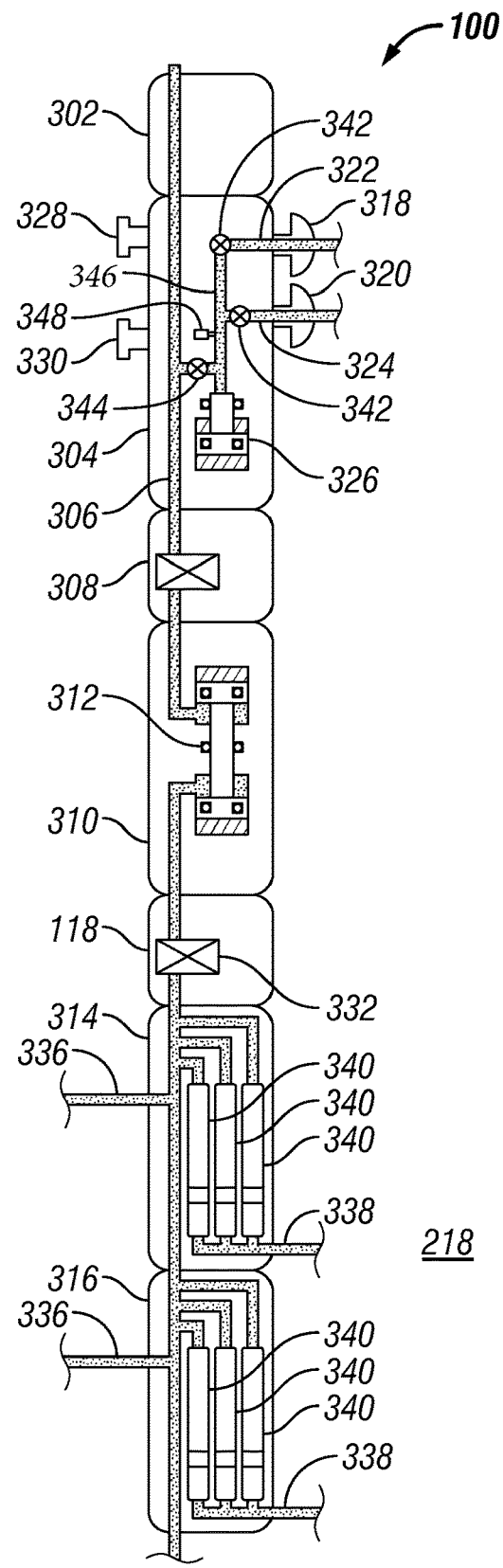
FIG. 3 is a schematic drawing of the formation testing tool.

FIG. 3 is a schematic of downhole fluid sampling tool 100, which may be used for fluid sampling operations and/or pressure test operations. In examples, downhole fluid sampling tool 100 includes a power telemetry section 302 through which the tool communicates with other actuators and sensors 116 in drill string 200 or conveyance 102 (e.g., referring to FIGS. 1 and 2), the drill string's telemetry section 302, and/or directly with a surface telemetry system (not illustrated). In examples, power telemetry section 302 may also be a port through which the various actuators (e.g. valves) and sensors (e.g., temperature and pressure sensors) in the downhole fluid sampling tool 100 may be controlled and monitored. In examples, power telemetry section 302 includes a computer that exercises the control and monitoring function. In one embodiment, the control and monitoring function is performed by a computer in another part of the drill string or wireline tool (not shown) or by information handling system 122 on surface 112 (e.g., referring to FIGS. 1 and 2).

In examples, downhole fluid sampling tool 100 includes a dual probe section 304, which extracts fluid from the reservoir and delivers it to a channel 306 that extends from one end of downhole fluid sampling tool 100 to the other. Without limitation, dual probe section 304 includes two probes 318, 320 which may extend from downhole fluid sampling tool 100 and press against the inner wall of wellbore 104 (e.g., referring to FIG. 1). Probe channels 322, 324 may connect probes 318, 320 to channel 306. The high-volume bidirectional pump 312 may be used to pump fluids from the reservoir, through probe channels 322, 324 and to channel 306. Alternatively, a low volume pump 326 may be used for this purpose. Two standoffs or stabilizers 328, 330 hold downhole fluid sampling tool 100 in place as probes 318, 320 press against the wall of wellbore 104. In examples, probes 318, 320 and stabilizers 328, 330 may be retracted when downhole fluid sampling tool 100 may be in motion and probes 318, 320 and stabilizers 328, 330 may be extended to sample the formation fluids at any suitable location in wellbore 104. Other probe sections include focused sampling probes, oval probes, or packers.

In examples, channel 306 may be connected to other tools disposed on drill string 200 or conveyance 102 (e.g., referring to FIGS. 1 and 2). In examples, downhole fluid sampling tool 100 may also include a quartz gauge section 308, which may include sensors to allow measurement of properties, such as temperature and pressure, of fluid in channel 306. Additionally, downhole fluid sampling tool 100 may include a flow-control pump-out section 310, which may include a high-volume bidirectional pump 312 for pumping fluid through channel 306. In examples, downhole fluid sampling tool 100 may include two multi-chamber sections 314, 316, referred to collectively as multi-chamber sections 314, 316 or individually as first multi-chamber section 314 and second multi-chamber section 316, respectively.

In examples, multi-chamber sections 314, 316 may be separated from flow-control pump-out section 310 by sensor section 332, which may house at least one sensor 334. Sensor 334 may be displaced within sensor section 332 in-line with channel 306 to be a "flow through" sensor. In alternate examples, sensor 334 may be connected to channel 306 via an offshoot of channel 306. Without limitation, sensor 334 may include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors, microfluidic sensors, selective electrodes such as ion selective electrodes, and/or combinations thereof. In examples, sensor 344 may operate and/or function to measure drilling fluid filtrate, discussed further below.

Additionally, multi-chamber section 314, 316 may comprise access channel 336 and chamber access channel 338. Without limitation, access channel 336 and chamber access channel 338 may operate and function to either allow a solids-containing fluid (e.g., mud) disposed in wellbore 104 in or provide a path for removing fluid from downhole fluid sampling tool 100 into wellbore 104. As illustrated, multi-chamber section 314, 316 may comprise a plurality of chambers 340. Chambers 340 may be sampling chamber that may be used to sample wellbore fluids, formation fluids, and/or the like during measurement operations. It should be noted that formation testing tool 100 may also be used in pressure testing operations.

For example, during pressure testing operations, probes 318, 320 may be pressed against the inner wall of wellbore 104 (e.g., referring to FIG. 1). Pressure may increase at probes 318, 320 due to formation 106 (e.g., referring to FIG. 1 or 2) exerting pressure on probes 318, 320. As pressure rises and reaches a predetermined pressure, valves 342 opens so as to close equalizer valve 344, thereby isolating fluid passageway 346 from the annulus 218. In this manner, valve 342 ensures that equalizer valve 344 closes only after probes 318, 320 has entered contact with mudcake (not illustrated) that is disposed against the inner wall of wellbore 104. In examples, as probes 318, 320 are pressed against the inner wall of wellbore 104, the pressure rises and closes the equalizer valve in fluid passageway 346, thereby isolating the fluid passageway 346 from the annulus 218. In this manner, the equalizer valve in fluid passageway 346 may close before probes 318, 320 may have entered contact with the mudcake that lines the inner wall of wellbore 104. Fluid passageway 346, now closed to annulus 218, is in fluid communication with low volume pump 326.

As low volume pump 326 is actuated, formation fluid may thus be drawn through probe channels 322, 324 and probes 318, 320. The movement of low volume pump 326 lowers the pressure in fluid passageway 346 to a pressure below the formation pressure, such that formation fluid is drawn through probe channels 322, 324 and probes 318, 320 and into fluid passageway 346. The pressure of the formation fluid may be measured in fluid passageway 346 while probes 318, 320 serves as a seal to prevent annular fluids from entering fluid passageway 346 and invalidating the formation pressure measurement.

With low volume pump 326 in its fully retracted position and formation fluid drawn into fluid passageway 346, the pressure will stabilize and enable pressure transducers 348 to sense and measure formation fluid pressure. The measured pressure is transmitted to information handling system 122 disposed on formation testing tool 100 and/or it may be transmitted to the surface via mud pulse telemetry or by any other conventional telemetry means to an information handling system 122 disposed on surface 112.

During this interval, pressure transducers 348 may continuously monitor the pressure in fluid passageway 346 until the pressure stabilizes, or after a predetermined time interval. When the measured pressure stabilizes, or after a predetermined time interval, for example at 1800 psi, and is sensed by pressure transducer 348 the drawdown operation may be complete. Once complete, fluid for the pressure test in fluid passageway 346 may be dispelled from formation testing tool 100 through the opening and/or closing of valves 342 and/or equalizer valve 344 as low volume pump 326 returns to a starting position.

During formation sampling operations, as described above, the acquisition of representative formation fluid samples may allow for proper reservoir management and development. However, because of overbalance pressure in the mud column, mud filtrate invades and contaminates the reservoir fluid during the drilling process, before the mudcake around the wellbore is properly formed. Although water-based mud (WBM) is immiscible with formation fluid, oil-based mud (OBM) is miscible with it. Samples with OBM contamination levels greater than at least 10% for oils and 3% for volatile oils and gas condensates may be considered unusable because the OBM contamination alters the formation fluid properties and phase behavior; this alteration prevents an accurate characterization of the reservoir fluid. General targets are below 5% contamination for oils, and below 2% contamination for volatile oils and less than 1% contamination for condensates.

During fluid sampling operations, it may be difficult to avoid contamination. It should be noted that open hole sampling is usually a single opportunity event. For example, after sample are acquired, as described above, the samples may be taken to a laboratory for analysis. After analysis is complete, it may not be possible to acquire additional samples. Consequently, during fluid sampling operations contaminated fluid may be cleaned up before taking a fluid sample. Cleanup times may depend on multiple parameters, including formation permeability, fluid viscosity, depth of invasion, and wellbore mud column overbalance pressure. Current methods for predicting contamination may rely on curve fitting to a single (in some cases multiple) property such as density or gas oil ratio ("GOR"). Curve fitting relies on the assumption that when the properties being monitored do not change significantly as the pumping continues, the contamination level is low. However, this may also be because of steady state effect even at high contamination level. Additionally, contamination value from curve fitting method may be sensitive to data selection and may depend on the endmember filtrate and formation fluid properties which may not be measured directly either downhole or in the laboratory.

During fluid sampling operations, a pressure test operation may be performed, which may aide in predicting contamination using density and formation properties such as drawdown mobility (or a transient mobility such as provided by exact mobility), formation pressure, overbalance, drawdown pressures, porosity etc. By combining multiple parameters such fluid density, drawdown mobility, formation pressure, drawdown and overbalance pressure, predicted contamination value from a pressure test, described above, clean fluid samples may be identified. Moreover, the workflow described below may not be dependent on end member properties. The workflow is based on constraining pumpout data with formation properties from pressure testing data. As an overview of the workflow, a large dataset of pumpout volume, density and formation properties data acquired from different regions of the world are used to develop a predictive model using for instance a machine learning approach. As noted below, the machine learning approach may also be performed by a mapping schemes that may allow for a prediction of output. For example, an output may be predicted based at least in part on the input. Without limitation, the density may be represented as optimized parameters of an inverse or a double exponential equation fitted to the density curve. The contamination estimation method has been validated with several dataset from different region of the world.

Figure 4:
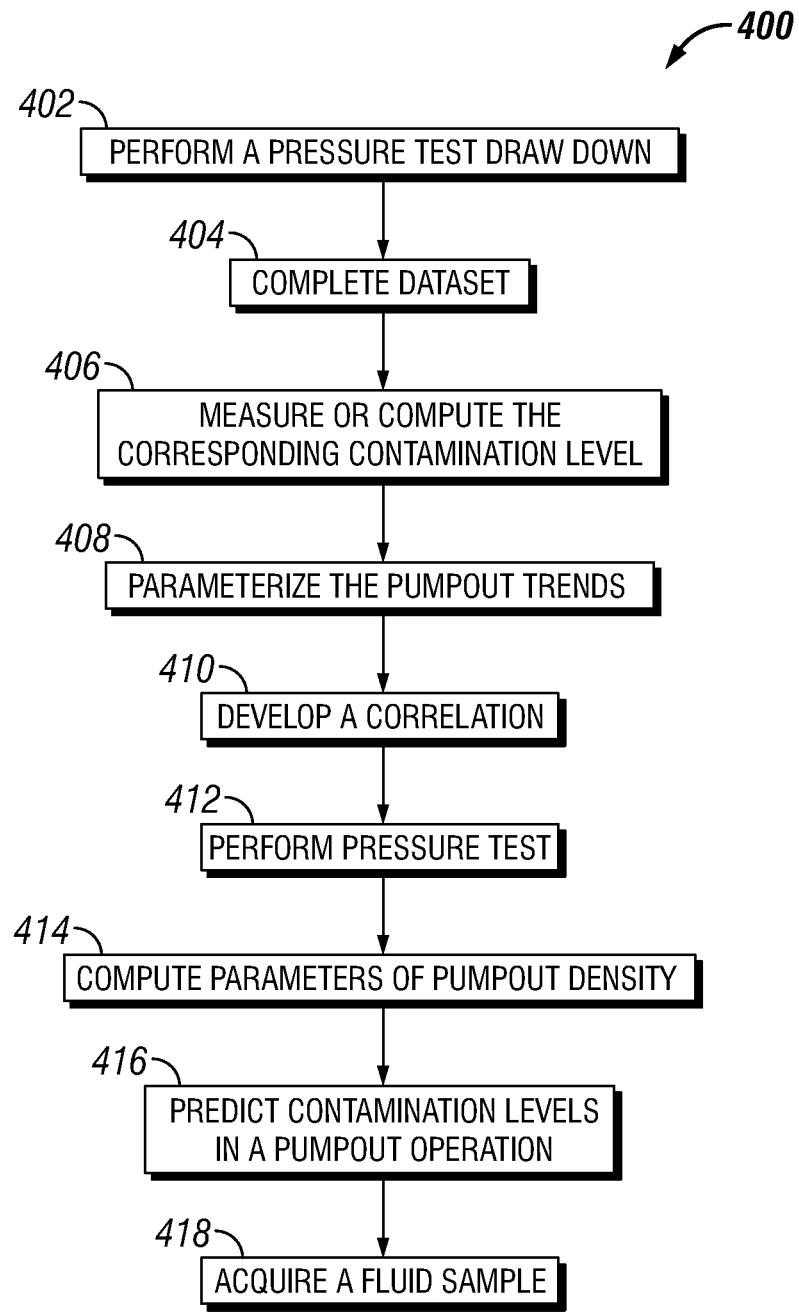
FIG. 4 is a flow chart for identifying a clean fluid sample.

As illustrated in FIG. 4, workflow 400 may combine pumpout data with the formation properties data obtained from pressure testing. Workflow 400 may begin with block 402. In block 402 a pressure test drawdown operation may be performed at a location of a formation pumpout operation. It should be noted that the pressure test drawdown operation may be performed within an area no larger than 2% away from the formation pumpout operation. During this operation, the pressure bled off prior to the drawdown may be recorded as a function of set pressure. In examples, a function of set pressure may be defined as monitoring changes in pressure to a control fluid. After bleeding off pressure prior to a drawdown, a pressure test operation may be performed.

In block 404, during the pressure test operations, a dataset may be compiled which may include formation properties including formation pressure, wellbore pressure, drawdown (or transient) mobility, drawdown pressure, blead off pressure (or other mud cake properties), pumpout volume, fluid formation fluid density and viscosity, filtrate density, and viscosity. These formation properties may be used to produce a contamination profile at the location (i.e., pumpout station) in which the pressure test operation and formation pumpout operations have taken place. In block 406, the corresponding contamination level may be measured and/or computed as a function of pumpout volume in captured samples from the corresponding pumpout stations. It should be noted that workflow 400 may be performed at any number of pumpout stations within the wellbore. In block 408, pumpout trends may be parameterized with at least one ubiquitous pumpout model such as but not limited to an inverse power law model as seen below:

$$\rho = A + B \times v_{-\rho} \quad (1)$$

For Equation (1), rho($\rho$) is the fluid density, v is the volume, A, B and $\beta$ are optimized parameters when an inverse pumpout model is used. Without limitation, the parameters for other models may be more than three variables. It should be noted that parameterizing the pumpout trends may include identifying how the trend is changing over time as fluid is being pumped out, where decaying exponential curves are trends that identify when fluid may become clean. Without limitation, other pumpout models that may be used in block 408 may be arctan pumpout models or double exponential models. In block 410, a correlation may be developed that may include, but is not limited to, methods of machine learning to the parameters of at least one of the pumpout trend model, formation properties, mud cake properties and fluid properties to contamination. It should be noted that block 410 may also utilize mapping schemes that may allow for a prediction of output. For example, an output may be predicted based at least in part on the input. Additionally, machine learning may de-spike measured data, smooth measured data, and/or remove outliers. The correlation may map the contamination at a certain area and may map any input value to the pumpout trend. Additionally, based on this input contamination of the fluid sample may be identified. It should be noted that the correlation may be produced as an index. In block 412, input data for the model may be captured and identified in real time. This is done to compute the formation properties such as formation pressure, drawdown mobility, difference between drawdown pressure and formation pressure and the overbalance pressure.

In block 414, downhole fluid sampling tool 100 (e.g., referring to FIG. 1) may acquire a fluid sample down hole. Additionally, downhole fluid sampling tool 100 may measure pumpout data including the accumulated volume and density. Additionally, downhole fluid sampling tool 100 may compute optimized parameters of the pumpout density trend using the selected pumpout trend model. It should be noted that the optimized parameters may be found and determined by fitting known shapes to shapes found in real time during the pumpout. This optimization may change the input to the inverse power trend. In block 416, measured and/or gathered input data including the formation properties and pumpout data, may be used in a correlation model to predict current contamination levels in the pumpout. Block 416 may determine when in time there will be clean formation fluid to take for a fluid sample. In block 418, a clean fluid sample may be taken, in part, based on the contamination level determined by workflow 400. It should be noted, an acceptably low contaminated fluid sample, or clean fluid sample, is defined differently for oils, volatile oils, and condensates. For example, an acceptably low contaminated fluid sample for oils is defined as having less than 5% contamination. For volatile oils, an acceptably low contaminated fluid sample is defined as having less than 2% contamination. For gas condensates, an acceptably low contaminated fluid sample is defined as having less than 1% contamination. According to McCain classification of reservoir oil, it should be noted that a black oil is defined as oil having GOR less than 1000 scf/stb, API less than 45 and oil FVF less than 2 (low shrinkage oil). A volatile oil is defined as oil with GOR between 1000 and 8000 scf/stb, API between 45 and 60 and oil FVF greater than 2 (high shrinkage oil) A gas condensate is defined as having GOR between 70000 and 100000, API greater than 60 and is generally light in color. An Oil-Based contaminate usually consist of C11-C29 components and will be dominated by paraffinic C14-C18 components. After a clean fluid sample is taken or a clean fluid samples cannot be taken, then downhole fluid sampling tool 100 may be moved to a new location and workflow 400 may be repeated.

Workflow 400 may improve current technology because current methods may only use pumpout data to predict contamination. Using a combination of formation properties and pumpout data to predict contamination may predict contamination with more accuracy and consistency compared with current density fitting method. For example, existing density fitting method using arc tan fitting method rely end member properties which are not measured directly in the laboratory or downhole. It should be noted that end member properties are the absolute clear property of a clean fluid sample. The end member properties are usually estimated as a range value. Workflow 400 (e.g., referring to FIG. 4) does not rely no endmember properties. Additionally, workflow 400 may not be sensitive to data selection while the existing methods show such sensitivity. Workflow 400 as identified above allows for the use of pumpout data and formation properties in predicting contamination level of fluid samples.

The preceding description provides various embodiments of systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

Statement 1. A method may comprise positioning a downhole fluid sampling tool into a wellbore; performing a pressure test operation within the wellbore; performing a pumpout operation within the wellbore; identifying when a clean fluid sample may be taken by the downhole fluid sampling tool from at least the pressure test operation and the pumpout operation; and acquiring the clean fluid sample from the wellbore.

Statement 2. The method of statement 1, further comprising compiling a dataset of one or more formation properties from the pressure test operation.

Statement 3. The method of statement 2, wherein the one or more formation properties include at least one of formation pressure, wellbore pressure, drawdown mobility, drawdown pressure, blead off pressure, pumpout volume, fluid density, or fluid viscosity.

Statement 4. The method of statements 1 or 2, further comprising measuring a contamination level of a fluid sample as a function of pumpout volume.

Statement 5. The method of statements 1, 2, or 4, further comprising parameterizing a pumpout trend of a formation fluid from the pumpout operation.

Statement 6. The method of statements 1, 2, 4, or 5, wherein the identifying when the clean fluid sample may be taken includes a mapping scheme or machine learning.

Statement 7. The method of statements 1, 2, or 4-6, further comprising predicting contamination levels of a formation fluid from a correlation model using one or more formation properties and pumpout data.

Statement 8. The method of statements 1, 2, or 4-7, further comprising developing a correlation between a pumpout trend model, one or more formation properties, mud cake properties, and formation fluid properties to determine contamination of a formation fluid.

Statement 9. The method of statements 1, 2, or 4-8, further comprising performing the pressure test and pumpout operation in real time.

Statement 10. The method of statements 1, 2, or 4-9, wherein the clean fluid sample is below 5% contamination for an oil, below 2% contamination for a volatile oil, or less than 1% for a condensate.

Statement 11. A system may comprise a downhole fluid sampling tool comprising: one or more probes attached to the downhole fluid sampling tool; one or more stabilizers attached to the downhole fluid sampling tool; and a sensor placed in the downhole fluid sampling tool configured to measure drilling fluid filtrate; an information handling machine configured to: identify when a clean fluid sample may be taken by the downhole fluid sampling tool from at least a pressure test operation and a pumpout operation.

Statement 12. The system of statement 11, wherein the information handling system is further configured to compile a dataset of one or more formation properties from the pressure test operation.

Statement 13. The system of statement 12, wherein the one or more formation properties are formation pressure, wellbore pressure, drawdown mobility, drawdown pressure, bleed off pressure, pumpout volume, fluid density, or fluid viscosity.

Statement 14. The system of statements 11 or 12, wherein the information handling system is further configured to measure a contamination level of a fluid sample as a function of pumpout volume.

Statement 15. The system of statements 11, 12, or 14, wherein the information handling system is further configured to parameterize a pumpout trend of a formation fluid from the pumpout operation.

Statement 16. The system of statements 11, 12, 14, or 15, wherein the identify when the clean fluid sample may be taken is performed by a mapping scheme or machine learning.

Statement 17. The system of statements 11, 12, or 14-16, wherein the information handling system is further configured to predict contamination levels of a formation fluid from a correlation model using one or more formation properties and pumpout data.

Statement 18. The system of statements 11, 12, or 14-17, wherein the information handling system is further configured to develop a correlation between a pumpout trend model, one or more formation properties, mud cake properties, and formation fluid properties to determine contamination of a formation fluid.

Statement 19. The system of statements 11, 12, or 14-18, wherein the information handling system is further configured to operate the downhole fluid sampling tool to perform the pressure test and the pumpout operation in real time.

Statement 20. The system of statements 11, 12, or 14-19, wherein the clean fluid sample is below 5% contamination for an oil, below 2% contamination for a volatile oil, or less than 1% for a condensate.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

Therefore, the present embodiments are well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Although individual embodiments are discussed, the disclosure covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method comprising:
    positioning a downhole fluid sampling tool into a wellbore;
    performing a pressure test operation within the wellbore;
    performing a pumpout operation within the wellbore;
    identifying when a clean fluid sample may be taken by the downhole fluid sampling tool from at least the pressure test operation and the pumpout operation;
    acquiring the clean fluid sample from the wellbore; and
    predicting contamination levels of a formation fluid from a correlation model using one or more formation properties and pumpout data.

2. The method of claim 1, further comprising compiling a dataset of one or more formation properties from the pressure test operation.

3. The method of claim 2, wherein the one or more formation properties include at least one of formation pressure, wellbore pressure, drawdown mobility, drawdown pressure, bleed off pressure, pumpout volume, fluid density, or fluid viscosity.

4. The method of claim 1, further comprising measuring a contamination level of a fluid sample as a function of pumpout volume.

5. The method of claim 1, further comprising parameterizing a pumpout trend of a formation fluid from the pumpout operation.

6. The method of claim 1, wherein the identifying when the clean fluid sample may be taken includes a mapping scheme or machine learning.

7. The method of claim 1, further comprising developing a correlation between a pumpout trend model, one or more formation properties, mud cake properties, and formation fluid properties to determine contamination of a formation fluid.

8. A method of claim 1, further comprising performing the pressure test and pumpout operation in real time.

9. The method of claim 1, wherein the clean fluid sample is below 5% contamination for an oil, below 2% contamination for a volatile oil, or less than 1% for a condensate.

10. The method of claim 1, wherein the downhole tool comprises:
    one or more probes;
    one or more stabilizers; and
    a sensor configured to measure drilling fluid filtrate.

11. A method comprising:
positioning a downhole fluid sampling tool into a wellbore, wherein the downhole tool comprises;
one or more probes;
one or more stabilizers; and
a sensor configured to measure drilling fluid filtrate;
performing a pressure test operation within the wellbore;
performing a pumpout operation within the wellbore;
identifying when a clean fluid sample may be taken by the downhole fluid sampling tool from at least the pressure test operation and the pumpout operation;
acquiring the clean fluid sample from the wellbore;
compiling a dataset of one or more formation properties from the pressure test operation wherein the one or more formation properties include at least one of formation pressure, wellbore pressure, drawdown mobility, drawdown pressure, bleed off pressure, pumpout volume, fluid density, or fluid viscosity;
parameterizing a pumpout trend of a formation fluid from the pumpout operation; and
predicting contamination levels of a formation fluid from a correlation model using one or more formation properties and pumpout data.

12. The method of claim 11, further comprising measuring a contamination level of a fluid sample as a function of pumpout volume.

13. The method of claim 11, wherein the identifying when the clean fluid sample may be taken includes a mapping scheme.

14. The method of claim 11, wherein the identifying when the clean fluid sample may be taken includes machine learning.

15. The method of claim 14, wherein the machine learning de-spikes the dataset.

16. The method of claim 11, further comprising developing a correlation between a pumpout trend model, one or more formation properties, mud cake properties, and formation fluid properties to determine contamination of a formation fluid.

17. The method of claim 11, further comprising performing the pressure test and pumpout operation in real time.

18. The method of claim 11, wherein the clean fluid sample is below 5% contamination for an oil, below 2% contamination for a volatile oil, or less than 1% for a condensate.

19. A method comprising:
positioning a downhole fluid sampling tool into a wellbore;
performing a pressure test operation within the wellbore;
performing a pumpout operation within the wellbore;
identifying when a clean fluid sample may be taken by the downhole fluid sampling tool from at least the pressure test operation and the pumpout operation;
acquiring the clean fluid sample from the wellbore; and
developing a correlation between a pumpout trend model, one or more formation properties, mud cake properties, and formation fluid properties to determine contamination of a formation fluid.

20. A method comprising:
positioning a downhole fluid sampling tool into a wellbore, wherein the downhole tool comprises;
one or more probes;
one or more stabilizers; and
a sensor configured to measure drilling fluid filtrate;
performing a pressure test operation within the wellbore;
performing a pumpout operation within the wellbore;
identifying when a clean fluid sample may be taken by the downhole fluid sampling tool from at least the pressure test operation and the pumpout operation wherein the identifying when the clean fluid sample may be taken includes machine learning;
acquiring the clean fluid sample from the wellbore;
compiling a dataset of one or more formation properties from the pressure test operation wherein the one or more formation properties include at least one of formation pressure, wellbore pressure, drawdown mobility, drawdown pressure, bleed off pressure, pumpout volume, fluid density, or fluid viscosity; and
parameterizing a pumpout trend of a formation fluid from the pumpout operation.

21. A method comprising:
positioning a downhole fluid sampling tool into a wellbore, wherein the downhole tool comprises;
one or more probes;
one or more stabilizers; and
a sensor configured to measure drilling fluid filtrate;
performing a pressure test operation within the wellbore;
performing a pumpout operation within the wellbore;
identifying when a clean fluid sample may be taken by the downhole fluid sampling tool from at least the pressure test operation and the pumpout operation wherein the identifying when the clean fluid sample may be taken includes machine learning which de-spikes the dataset;
acquiring the clean fluid sample from the wellbore;
compiling a dataset of one or more formation properties from the pressure test operation wherein the one or more formation properties include at least one of formation pressure, wellbore pressure, drawdown mobility, drawdown pressure, bleed off pressure, pumpout volume, fluid density, or fluid viscosity; and
parameterizing a pumpout trend of a formation fluid from the pumpout operation.

22. A method comprising:
positioning a downhole fluid sampling tool into a wellbore, wherein the downhole tool comprises;
one or more probes;
one or more stabilizers; and
a sensor configured to measure drilling fluid filtrate;
performing a pressure test operation within the wellbore;
performing a pumpout operation within the wellbore;
identifying when a clean fluid sample may be taken by the downhole fluid sampling tool from at least the pressure test operation and the pumpout operation;
acquiring the clean fluid sample from the wellbore;
compiling a dataset of one or more formation properties from the pressure test operation wherein the one or more formation properties include at least one of formation pressure, wellbore pressure, drawdown mobility, drawdown pressure, bleed off pressure, pumpout volume, fluid density, or fluid viscosity;
parameterizing a pumpout trend of a formation fluid from the pumpout operation; and
developing a correlation between a pumpout trend model, one or more formation properties, mud cake properties, and formation fluid properties to determine contamination of a formation fluid.

* * * * *